US012597491B2

(12) United States Patent (10) Patent No.: US 12,597,491 B2
Song et al. (45) Date of Patent: Apr. 7, 2026

(54) METHOD AND APPARATUS FOR COMPRESSING FASTQ DATA THROUGH CHARACTER FREQUENCY-BASED SEQUENCE REORDERING

(71) Applicant: Pusan National University Industry-University Cooperation Foundation, Busan (KR)

(72) Inventors: Giltae Song, Busan (KR); Dohyeon Lee, Busan (KR)

(73) Assignee: Pusan National University Industry-University Cooperation Foundation, Busan (KR)

( * ) Notice: Subject to any disclaimer, the term of this patent is extended or adjusted under 35 U.S.C. 154(b) by 1137 days.

(21) Appl. No.: 17/536,046

(22) Filed: Nov. 28, 2021

(65) Prior Publication Data

US 2022/0199202 A1 Jun. 23, 2022

(30) Foreign Application Priority Data

Dec. 21, 2020 (KR) ........................ 10-2020-0179632

(51) Int. Cl.
*G01N 33/48* (2006.01)
*G06F 16/174* (2019.01)
*G16B 50/50* (2019.01)

(52) U.S. Cl.
CPC ......... *G16B 50/50* (2019.02); *G06F 16/1744* (2019.01)

(58) Field of Classification Search
None
See application file for complete search history.

(56) References Cited

PUBLICATIONS

Lee, Dohyeon, and Giltae Song. "FastqCLS: a FASTQ compressor for long-read sequencing via read reordering using a novel scoring model." Bioinformatics 38.2 (2022): 351-356.*
Dohyeon Lee, FASTQ compression method based on the reordering by character frequency, Aug. 1, 2020.
Bonfield, J. K., & Mahoney, M. V. (2013). Compression of FASTQ and SAM format sequencing data. PloS one, 8(3).

* cited by examiner

*Primary Examiner* — Anna Skibinsky

(74) *Attorney, Agent, or Firm* — David L. Nocilly; Bond Shoeneck & King PLLC

(57) ABSTRACT

A method and apparatus for decompressing FASTQ data through character frequency-based sequence reordering implemented by a computer apparatus, the method including separating genome sequencing data into components of an identifier, a nucleotide sequence read, and prediction quality information; measuring character frequency for the entire data of each of the nucleotide sequence read and the prediction quality information; producing a score by applying the measured character frequency for the nucleotide sequence read and the prediction quality information; reordering the nucleotide sequence read and the prediction quality information based on a condition that is preset based on the score; and compressing at least one of information of the identifier, an identifier of the nucleotide sequence read, and an identifier of the prediction quality information through a compression program by including the reordered nucleotide sequence read and the reordered prediction quality information and generating compressed genome sequencing data.

19 Claims, 13 Drawing Sheets

<u>110</u>

730 →

2342152535 20
4322353020 15
4006400000 60
4402403500 15
1460054055 00
4520354520 00
4007350000 65
0550050505 00
1640055540 00
1550054550 00

720 →

710 →

Index of base

METHOD AND APPARATUS FOR COMPRESSING FASTQ DATA THROUGH CHARACTER FREQUENCY-BASED SEQUENCE REORDERING

CROSS-REFERENCE TO RELATED APPLICATION

This application claims the priority benefit of Korean Patent Application No. 10-2020-0179632, filed on Dec. 21, 2020, in the Korean Intellectual Property Office, the disclosure of which is incorporated herein by reference.

BACKGROUND OF THE INVENTION

1. Field of the Invention

Example embodiments of the following description relate to a dedicated compression technology for efficiently storing and transmitting FASTQ data that is a representative format of genomic data, and more particularly, to a method and apparatus for compressing FASTQ data through a character frequency-based sequence reordering.

2. Description of the Related Art

Genome sequencing data is rapidly increasing due to a reduction in production cost and development of a cell analysis scheme by Next Generation Sequencing (NGS) technology. Due to the NGS technology that appeared in 2008, production capacity of genome sequencing data is improving. With the advent of 3G and 4G sequencing technologies and single cell analysis that appeared since then, the production capacity of genome sequencing data is doubling every 7 months beyond Moore's law. Due to this trend, it is estimated that genome sequencing data will enter the realm of bigdata along with texts and images by 2025. As a result, cost of storing and transmitting the genome sequencing data becomes an issue.

Although some general-purpose compression techniques are applied to outperform the above issue, the general-purpose compression techniques have a degraded compression ratio since genome sequencing data is stored in a special format. To solve this, compression programs dedicated for genome sequencing are developing a novel method using the following structure of genome sequencing data.

The genome sequencing data uses FASTQ as a text-based format for storing nucleotide sequences and quality scores corresponding thereto, and includes ASCII characters. In general, the FASTQ uses 4 lines per nucleotide sequence. Line 1 starts with '@' and includes a nucleotide sequence identifier and an additional explanation and line 2 generally includes alphabetical characters (A, C, T, G, N) as nucleotide sequence read information, but may be displayed in a form of a number (0, 1, 2, 3) according to a device. Line 3 starts with '+' and may include the same data as that of line 1. Line 4 refers to a quality value for the nucleotide sequence read of line 2 and uses Phred quality score as accuracy of a base. If Q=10, the accuracy of the base indicates 90% and if Q=20, the accuracy of the base indicates 99%. The higher a value of Q, the more accurate the output base. This value is displayed in ASCII code and generally displayed as 40 types of letters. However, recently, devices that express four types of letters are appearing.

Existing genome sequencing compression programs using the above features compress genome sequencing data into consideration of each component, an identifier, a nucleotide sequence read, and distribution and meaning of prediction quality scores. However, with the recent development of new sequencing technology, types of data have increased as a length of data varies and production platforms are diversified. Due to a change in data, the existing genome sequence compression program may not operate depending on a size of data and a type of a production platform.

As described above, although FASTQ data is widely used as a representative standard format of genomic data, capacity of the FASTQ data is very large and storage is not easy accordingly and cost of storage is very high. Although there are existing technologies to reduce compression capacity to outperform the above issue, the existing technologies simply use an overlapping ratio of nucleotide sequences and a compression ratio is not high. Also, prediction quality information of data called a quality value may be compressed to not be decompressed in order to increase a compression ratio. Therefore, a compression method dedicated for genome sequencing data that stably operates regardless of a variety of data is required.

BRIEF SUMMARY OF THE INVENTION

Example embodiments provide a method and apparatus for compressing FASTQ data through a character frequency-based sequence reordering, and more particularly, provide compression technology dedicated for genome sequencing data that stably operates in a variety of genome sequencing data and exhibits excellent performance for recent generated data.

Example embodiments provide a method and apparatus for compressing FASTQ data through a character frequency-based sequence reordering that may perform lossless compression on prediction quality information called a quality value and improve a compression ratio accordingly and may prevent damage of quality of data itself by improving the compression ratio using a new reordering scheme based on character frequency of a nucleotide sequence instead of using an overlapping ratio of nucleotide sequences or a lexicographic order scheme.

According to an aspect of at least one example embodiment, there is provided a method of compressing FASTQ data through character frequency-based sequence reordering implemented by a computer apparatus, the method including separating genome sequencing data into components of an identifier, a nucleotide sequence read, and prediction quality information; measuring character frequency for the entire data of each of the nucleotide sequence read and the prediction quality information; producing a score by applying the measured character frequency for the nucleotide sequence read and the prediction quality information; reordering the nucleotide sequence read and the prediction quality information based on a condition that is preset based on the score; and compressing at least one of information of the identifier, an identifier of the nucleotide sequence read, and an identifier of the prediction quality information through a compression program by including the reordered nucleotide sequence read and the reordered prediction quality information and generating compressed genome sequencing data.

The separating of the genome sequencing data may include separating again the identifier into a unique number of the identifier and additional information of the identifier, and the additional information of the identifier may be used as information of the identifier when performing compression through the compression program to generate the compressed genome sequencing data.

The measuring of the character frequency may include measuring a letter distribution for the entire data of each of the nucleotide sequence read and the prediction quality information and excluding a corresponding letter if the measured letter distribution is below a threshold.

The producing of the score may include measuring character frequency for a single nucleotide sequence read and producing a score; and repeating scoring for all nucleotide sequence reads including repetition of the single nucleotide sequence read.

The producing of the score may include measuring character frequency for single prediction quality information and producing a score; and repeating scoring for all prediction quality information including repetition of the single prediction quality information.

The producing of the score may include producing a score based on at least one of priority information and exclusion target information obtained through the measured character frequency for the nucleotide sequence read and the prediction quality information, and producing a score using all a letter distribution value that is character frequency information and a distribution value that is obtained by rounding the letter distribution value.

The reordering of the nucleotide sequence read and the prediction quality information may include combining the all nucleotide sequence reads with the respective corresponding identifiers and performing lexicographic order based on the produced score.

The reordering of the nucleotide sequence read and the prediction quality information may include combining the prediction quality information with the identifier and performing lexicographic order based on the produced score.

The generating of the compressed genome sequencing data may include storing the reordered nucleotide sequence read in combination with an identifier of the nucleotide sequence read through the compression program to remember order and storing the reordered prediction quality information in combination with an identifier of the prediction quality information through the compression program.

The FASTQ data compression method may further include decompressing the compressed genome sequencing data through the compression program; reordering the decompressed all nucleotide sequence reads and all prediction quality information based on the respective corresponding identifiers; and producing original genome sequencing data by separating and then combining the reordered all nucleotide sequence reads and all prediction quality information from the respective corresponding identifiers.

According to another aspect of at least one example embodiment, there is provided an apparatus for compressing FASTQ data through character frequency-based sequence reordering implemented by a computer apparatus, the apparatus including a genome sequencing data separator configured to separate genome sequencing data into components of an identifier, a nucleotide sequence read, and prediction quality information; a character frequency measurer configured to measure character frequency for the entire data of each of the nucleotide sequence read and the prediction quality information; a score producer configured to produce a score by applying the measured character frequency for the nucleotide sequence read and the prediction quality information; a score-based sorter configured to reorder the nucleotide sequence read and the prediction quality information based on a condition that is preset based on the score; and a genome sequencing data compressor configured to compress at least one of information of the identifier, an identifier of the nucleotide sequence read, and an identifier of the prediction quality information through a compression program by including the reordered nucleotide sequence read and the reordered prediction quality information and to generate compressed genome sequencing data.

The genome sequencing data separator may be configured to separate again the identifier into a unique number of the identifier and additional information of the identifier, and the additional information of the identifier may be used as information of the identifier when performing compression through the compression program to generate the compressed genome sequencing data.

The character frequency measurer may be configured to measure a letter distribution for the entire data of each of the nucleotide sequence read and the prediction quality information and excluding a corresponding letter if the measured letter distribution is below a threshold.

The score producer may be configured to measure character frequency for a single nucleotide sequence read and produce a score, and to repeat scoring for all nucleotide sequence reads including repetition of the single nucleotide sequence read.

The score producer may be configured to measure character frequency for single prediction quality information and produce a score, and to repeat scoring for all prediction quality information including repetition of the single prediction quality information.

The score producer may be configured to produce a score based on at least one of priority information and exclusion target information obtained through the measured character frequency for the nucleotide sequence read and the prediction quality information, and to produce a score using all a letter distribution value that is character frequency information and a distribution value that is obtained by rounding the letter distribution value.

The score-based sorter may be configured to combine the all nucleotide sequence reads with the respective corresponding identifiers and to perform lexicographic order based on the produced score.

The score-based sorter may be configured to combine the prediction quality information and the identifier and to perform lexicographic order based on the produced score.

The genome sequencing data compressor may be configured to store the reordered nucleotide sequence read in combination with an identifier of the nucleotide sequence read through the compression program to remember order and to store the reordered prediction quality information in combination with an identifier of the prediction quality information through the compression program.

The FASTQ data compression apparatus may further include a genome sequencing data decompressor configured to decompress the compressed genome sequencing data through the compression program, to reorder the decompressed all nucleotide sequence reads and all prediction quality information based on the respective corresponding identifiers, and to produce original genome sequencing data by separating and then combine the reordered all nucleotide sequence reads and all prediction quality information from the respective corresponding identifiers.

According to example embodiments, there may be provided a method and apparatus for compressing FASTQ data through a character frequency-based sequence reordering that may perform lossless compression on prediction quality information called a quality value and improve a compression ratio accordingly and may prevent damage of quality of data itself by improving the compression ratio using a new reordering scheme based on character frequency of nucleotide sequence instead of using an overlapping ratio of nucleotide sequences or a dictionary-type reordering scheme.

Further areas of applicability will become apparent from the description provided herein. The description and specific examples in this summary are intended for purposes of illustration only and are not intended to limit the scope of the present disclosure.

BRIEF DESCRIPTION OF THE SEVERAL VIEWS OF THE DRAWING(S)

These and/or other aspects, features, and advantages of the invention will become apparent and more readily appreciated from the following description of embodiments, taken in conjunction with the accompanying drawings of which:

DETAILED DESCRIPTION OF THE INVENTION

Figure 1:
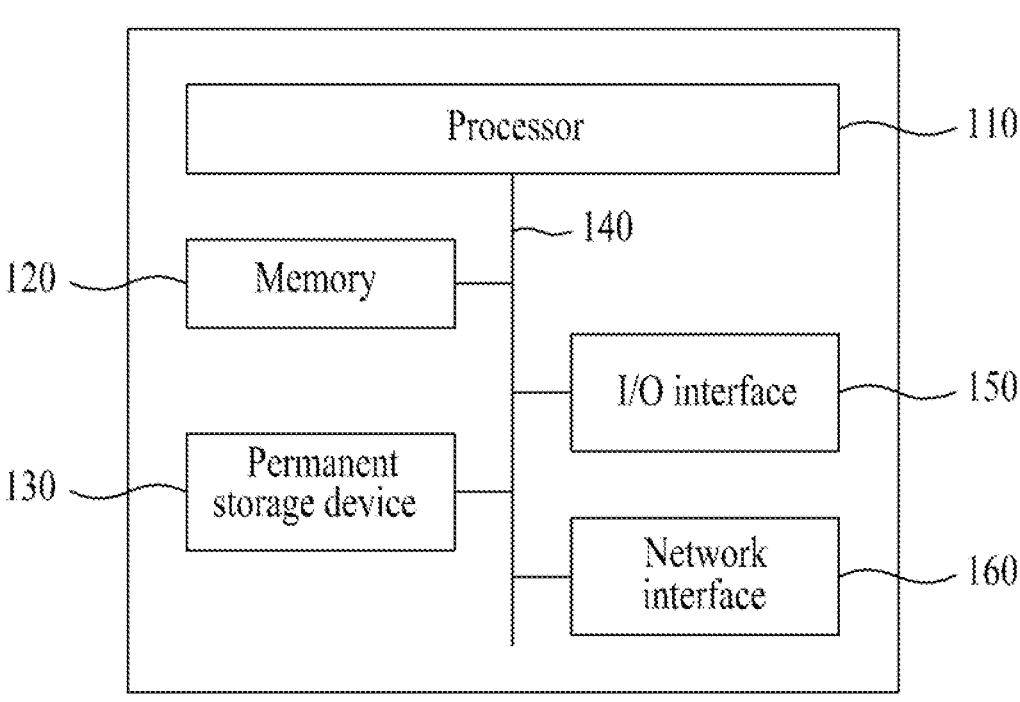
FIG. 1 is a diagram illustrating an example of a configuration of a computer system (apparatus) according to an example embodiment.

Hereinafter, some example embodiments will be described in detail with reference to the accompanying drawings. The following detailed structural or functional description of example embodiments is provided as an example only and various alterations and modifications may be made to the example embodiments. Accordingly, the example embodiments are not construed as being limited to the disclosure and should be understood to include all changes, equivalents, and replacements within the technical scope of the disclosure.

The terminology used herein is for describing various example embodiments only, and is not to be used to limit the disclosure. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Terms, such as first, second, and the like, may be used herein to describe components. Each of these terminologies is not used to define an essence, order or sequence of a corresponding component but used merely to distinguish the corresponding component from other components). For example, a first component may be referred to as a second component, and similarly the second component may also be referred to as the first component, without departing from the scope of the disclosure.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Hereinafter, example embodiments will be described with reference to the accompanying drawings. However, the example embodiments may be modified in various forms and the scope of the disclosure is not limited by the following example embodiments. In addition, some example embodiments are provided to further completely explain the disclosure for those skilled in the art. Shapes and sizes, etc., of components in the drawings may be exaggerated for further clear explanation.

Due to next generation sequencing (NGS), genome sequencing data has an increased size and includes many overlapping portions. Therefore, an amount of time and cost used to store and transmit the genome sequencing data increases. Although many data-only compression programs are studied to solve the above issues, they do not properly work on modified data due to the advent of new sequencing and analysis technology.

The present disclosure is conceived to solve the aforementioned issues found in the related art and may improve a compression ratio using a new reordering scheme (e.g., based on character frequency of a nucleotide sequence) instead of using an overlapping ratio of a nucleotide sequence or lexicographic order scheme. In the case of adopting this scheme, prediction quality information of data called a quality value may be compressed without loss and the compression ratio may be improved and quality of data itself may not be damaged accordingly.

The example embodiments are provided to properly work on genome sequencing data having a long nucleotide sequence (long-read) that has newly appeared. The example embodiments are based on order, which is similar to that of the existing genome sequencing data compression program, but differ in that reordering is performed using character frequency of a nucleotide sequence instead of using an overlapping portion. Here, various types of data were used as benchmark data and were verified to well work regardless of a size and a length of a nucleotide sequence. In particular, in the case of long nucleotide sequencing data, higher compression performance is observed compared to other compression programs.

Most genome sequencing data-only compression schemes internally use a general compression scheme. Performance of each program depends on a data preprocessing process. Basically, a preprocessing process of genome sequencing data starts with a separation process into components of a FASTQ format. Next, the preprocessing process improves compression performance through additional preprocessing processes, such as tokenization of an identifier (read-identifier tokenization), bit encoding of a nucleotide sequence read (bit nucleotide encoding), a reference genome comparison scheme of the nucleotide sequence read, loss compression of prediction quality information (quality score) about the nucleotide sequence read, and reordering of the entire nucleotide sequence.

Each identifier has a unique value for each nucleotide sequence. Also, additional information, such as a device name, an execution identifier, and tile coordinates used to generate the data may be recorded in an identifier area. The information may be similar or duplicated in all the nucleotide sequences. Such unnecessary duplicate information may cause genome sequencing data capacity to increase. To solve this, identifiers are separated into a more detailed area (tokens), which is referred to as tokenization of an identifier. The identifier area is separated by point (.), underscore (_), space ( ), affix (-), colon (:), equals (=), and deflected (/). Through this method, unnecessarily duplicate tokens are removed and compression performance is improved through delta encoding or run-length encoding. This method is used by programs LFastqC, LFQC, DSRC2, FQC, and Fastqz.

Most of a nucleotide sequence read may include bases A, C, G, and T, or may additionally use base N. Therefore, the nucleotide sequence read is expressed by using not a byte but a bit for each base. This approach is not currently used to improve a compression ratio since a general compression scheme basically includes entropy encoding. However, there is a study to effectively improve a compression ratio using the same. Since this program is produced for a more stable and high compression ratio rather than a compression speed, a bit encoding method is not used.

In the case of genome sequencing data, reference genome is present. The reference genome is data that minimizes rare variation with multiple sequence composites not a single nucleotide sequence, a hypothetical complete nucleotide sequence representing a species. Comparing the separated nucleotide sequence to the completed reference genome, there are many similarities. Using this, the approach compresses data by recording a position of reference genome similar to the separated nucleotide sequence and also separately recording a difference. However, this approach has an issue of storing reference genome with compressed data, restoring the reference genome improperly when the reference genome changes. Although the recent study uses a method of generating and using virtual reference genome using genome sequencing data, it is slow. Therefore, the current study prefers loss compression of prediction quality information or reordering rather than the aforementioned approaches.

The prediction quality information may be displayed using a number of letters greater than that of the nucleotide sequence read and may not be readily compressed due to a difference for each device that produces data. Therefore, the existing compression program regards that compressing the prediction quality information is an important factor to reduce capacity of genome sequencing data. The prediction quality information may be mixed with noise in the process of generating genome sequencing data and may express similar values for adjacent scores. Due to this feature, there is a study that the existing prediction quality information is not perfect and although new prediction quality information combined with a loss compression scheme is used, it does not affect a subsequent study. A binary threshold method expresses a quality value in a specific byte pattern If prediction quality information is higher than 30, and otherwise, expresses a quality value as 2. Also, there is a study that uses a method of replacing prediction quality information having low frequency with prediction quality information having high frequency using frequency of prediction quality information of the entire genome sequencing data. In addition, a program using a loss compression of prediction quality information uses a method, such as, for example, RQS, QVZ, QualComp, BEETL, and PBlock. This method may improve a compression ratio in previous generated data, but may be not required for recent generated short nucleotide sequencing data (short-read) since the loss compression scheme is applied.

Results of HiSeq 2000 having generated a short nucleotide sequence in the past are variously distributed ranging from 2 to 40. However, NovaSeq 6000 generating a recent short nucleotide sequence uses four or less letters. Therefore, a loss compression scheme of SPRING that is one of genome-only compression programs may improve performance of a compression ratio in past HiSeq 2000 data, but show insignificant performance in recent NovaSeq 6000 data.

In the case of genome sequencing data stored in a FASTQ format, order of a nucleotide sequence is randomly determined and thus, a high compression ratio may be obtained through reordering. This approach may be efficient and enhance locality of data if a nucleotide sequence read of genome sequencing data is largely duplicated and thus, may show good performance in a general compression scheme based on LZ-77. There is a binary threshold method that expresses a compression using reordering as a pattern of genome sequencing data and expresses as 2 if low. Also, there is a study that uses a method of replacing prediction quality information having low frequency with prediction quality information having high frequency using frequency of prediction quality information of the entire genome sequencing data. In addition, a program using a loss compression of prediction quality information uses a method, such as, for example, RQS, QVZ, QualComp, BEETL, and PBlock. This method may improve a compression ratio in previous generated data, but may be not required for recent generated short nucleotide sequencing data (short-read) since the loss compression scheme is applied.

Results of HiSeq 2000 having generated a short nucleotide sequence in the past are variously distributed ranging from 2 to 40. However, NovaSeq 6000 generating a recent short nucleotide sequence uses four or less letters. Therefore, a loss compression scheme of SPRING that is one of genome-only compression programs may improve performance of a compression ratio in past HiSeq 2000 data, but show insignificant performance in recent NovaSeq 6000 data.

In the case of genome sequencing data stored in a FASTQ format, order of a nucleotide sequence is randomly determined and thus, a high compression ratio may be obtained through reordering. This approach may be efficient and enhance locality of data if a nucleotide sequence read of genome sequencing data is largely duplicated and thus, may show good performance in a general compression scheme based on LZ-77. A compression using reordering shows good performance in benchmark data provided from MPEG HTS that proceeds with standardization of genome sequencing data.

However, there are limitations that the existing researches do not properly work on modified data due to development of new technology and do not properly work if a size of data increases due to the appearance of 3G sequencing technology and analysis of cancer genome sequencing data. Representatively, it is verified that LFastqC and LFQC do not properly operate for samples greater than or equal to 17,696 MB.

Due to appearance of various platforms, they may not operate if a structure of genome sequencing data varies. Representatively, SPRING does not compress a SOLiD type since the SOLiD type is expressed as 0, 1, 2, 3 not A, C, G, T. Therefore, issues found in the existing schemes are to be solved.

FIG. 1 is a diagram illustrating an example of a configuration of a computer system (apparatus) according to an example embodiment. For example, a FASTQ data compression apparatus according to example embodiments may be implemented through a computer system 100 of FIG. 1. Referring to FIG. 1, the computer system 100 may include, as components to perform a FASTQ data compression method, a processor 110, a memory 120, a permanent storage device 130, a bus 140, an input/output (I/O) interface 150, and a network interface 160.

The processor 110 may include any device capable of processing a sequence of instructions or a part thereof. The processor 110 may include, for example, a computer processor, a processor in a mobile device or another electronic device and/or a digital processor. The processor 110 may be included in, for example, a server computing device, a server computer, a series of server computers, a server farm, a cloud computer, a content platform, a mobile computing device, a smartphone, a tablet, a set-top box, and a media player. The processor 110 may be connected to the memory 120 through the bus 140.

The memory 120 may include a volatile memory, a permanent memory, a virtual memory, or other memories to store information used by the computer system 100 or output from the computer system 100. The memory 120 may include, for example, random access memory (RAM) and/or dynamic RAM (DRAM). The memory 120 may be used to store random information such as state information of the computer system 100. The memory 120 may be used to store instructions of the computer system 100 that include instructions for compressing, for example, FASTQ data. The computer system 100 may include at least one processor 110 if necessary or if appropriate.

The bus 140 may include a communication-based structure that enables interaction between various components of the computer system 100. The bus 140 may convey data between components of the computer system 100, for example, between the processor 110 and the memory 120. The bus 140 may include a wired and/or wireless communication medium between the components of the computer system 100 and may include parallel, serial, or other topology arrangements.

The permanent storage device 130 may include components such as a memory or another permanent storage device as used by the computer system 100 to store data during a predetermined extended period (e.g., compared to the memory 120). The permanent storage device 130 may include a non-volatile main memory as used by the processor 110 in the computer system 100. The permanent storage device 130 may include, for example, a flash memory, a hard disk, an optical disc, or other computer-readable record media.

The I/O interface 150 may include interfaces for a keyboard, a mouse, a voice instruction input, a display, or another input or output device. Configuration instructions and/or information for compression of FASTQ data may be received through the I/O interface 150.

The network interface 160 may include at least one interface for networks such as a local area network or the Internet. The network interface 160 may include interfaces for wired or wireless accesses. The configuration instructions and/or information for compression of FASTQ data may be received through the network interface 160.

Also, according to other example embodiments, the computer system 100 may include a number of components greater than a number of components shown in FIG. 1. However, there is no need to clearly illustrate most components according to the related art. For example, the computer system 100 may be configured to include at least a portion of I/O devices connected to the I/O interface 150 or may further include other components such as a transceiver, a global positioning system (GPS) module, a camera, various types of sensors, and a database.

The following example embodiments propose a method that stably operates although a size of data or a production platform varies and, to this end, provide a FASTQ_CLS (Compressor for Long-read Sequencing) program. Here, the FASTQ_CLS program may be included in a FASTQ data compression apparatus or may include the FASTQ data compression apparatus. Also, the FASTQ data compression apparatus and the components of the FASTQ data compression apparatus may perform operations 311 to 315 included in a FASTQ data compression method of FIG. 3, and may perform operations 321 to 323 corresponding to a decompression method.

Figure 2:
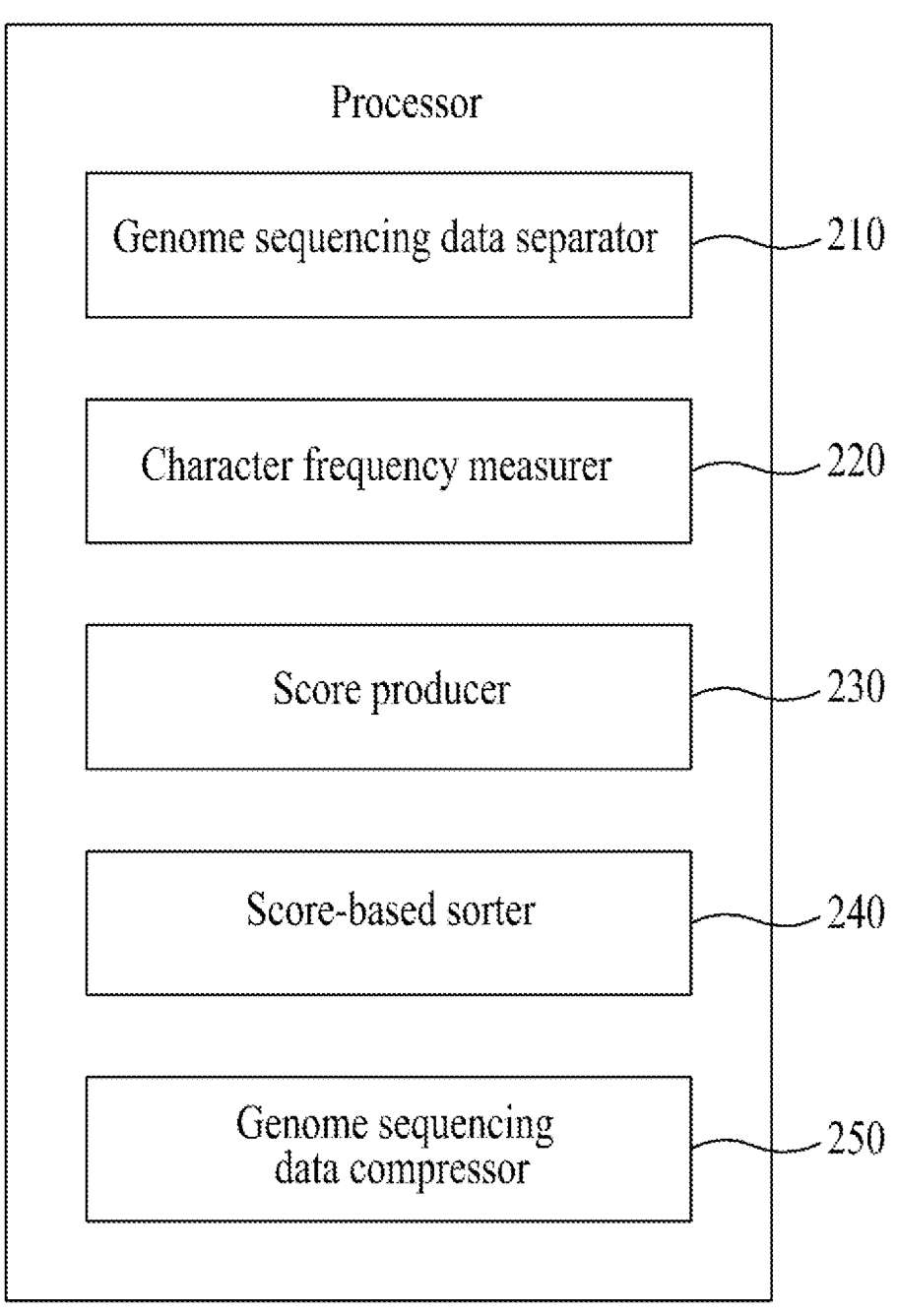
FIG. 2 is a diagram illustrating an example of a FASTQ data compression apparatus according to an example embodiment.

FIG. 2 is a diagram illustrating an example of a FASTQ data compression apparatus according to an example embodiment.

FIG. 2 illustrates an example of a component includable in the processor 110 of the computer system 100 of FIG. 1. Here, the processor 110 of the computer system 100 may include a FASTQ data compression apparatus. Referring to FIG. 2, the FASTQ data compression apparatus may include a genome sequencing data separator 210, a character frequency measurer 220, a score producer 230, a score-based sorter 240, and a genome sequencing data compressor 250. Also, depending on example embodiments, the FASTQ data compression apparatus may further include a decompressor.

Figure 3:
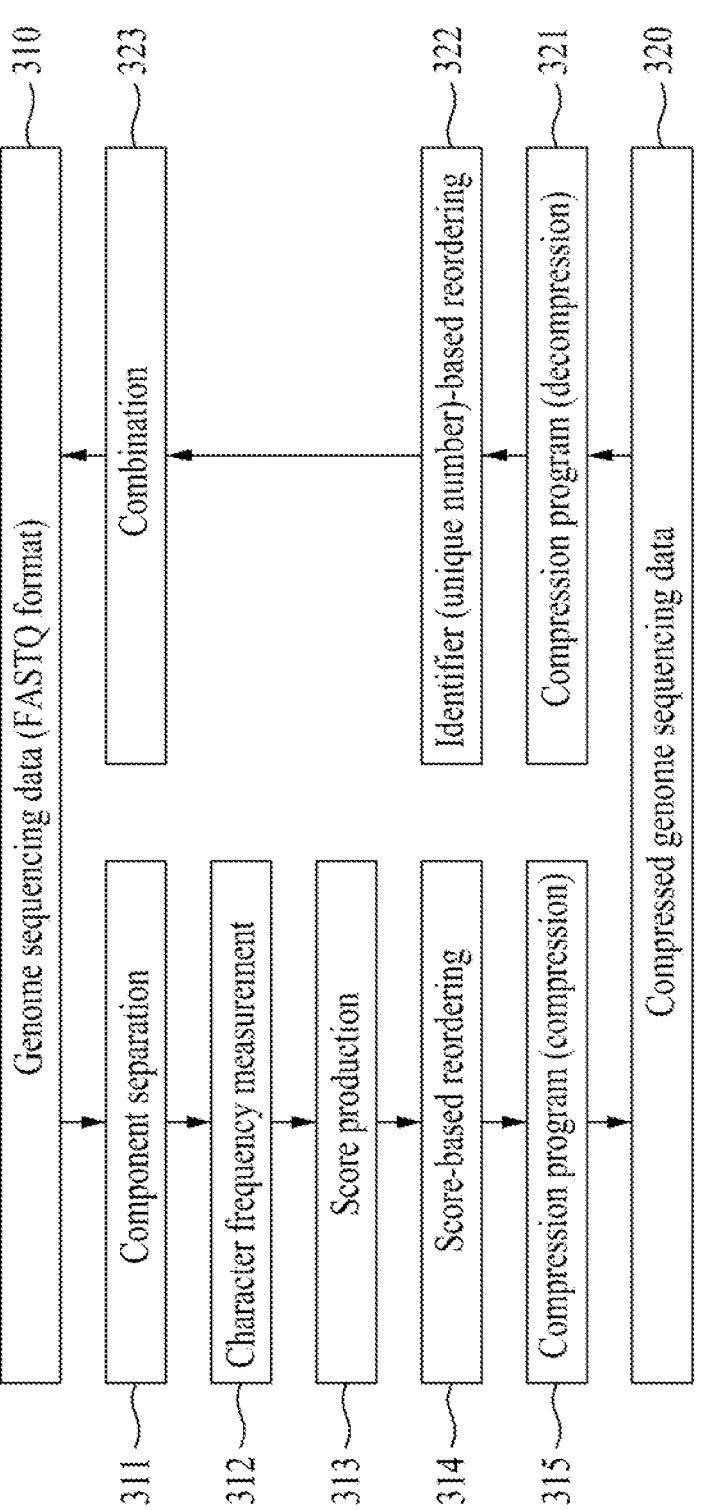
FIG. 3 illustrates an example of a FASTQ data compression method according to an example embodiment.

The processor 110 and the components of the processor 110 may perform operations 311 to 315 included in the FASTQ data compression method of FIG. 3. Also, the processor 110 and the components of the processor 110 may perform operations 321 to 323 corresponding to the decompression method. For example, the processor 110 and the components of the processor 110 may be implemented to execute an instruction according to at least one program code and a code of an OS included in the memory 120. Here, the at least one program code may correspond to a code of a program implemented to process the FASTQ data compression method.

The FASTQ data compression method may not be performed in illustrated order and a portion of operations may be omitted or an additional process may be further included.

FIG. 3 illustrates an example of a FASTQ data compression method according to an example embodiment.

Referring to FIG. 3, this program FASTQ_CLS may internally use a compression program and may improve compression performance through a data preprocessing process.

The FASTQ data compression method through character frequency-based sequence reordering implemented by a computer apparatus may include operation 311 of separating genome sequencing data 310 into components of an identifier, a nucleotide sequence read, and prediction quality information, operation 312 of measuring character frequency for the entire data of each of the separated nucleotide sequence read and prediction quality information, operation 313 of producing a score by applying the measured character frequency for the nucleotide sequence read and the prediction quality information, operation 314 of reordering the nucleotide sequence read and the prediction quality information based on a condition that is preset based on the score, and operation 315 of compressing at least one of information of the identifier, an identifier of the nucleotide sequence read, and an identifier of the prediction quality information through a compression program, for example, a compression program by including the reordered nucleotide sequence read and the reordered prediction quality information and generating compressed genome sequencing data 320.

Also, the FASTQ data compression method may further include operation 321 of decompressing the compressed genome sequencing data 320 through the compression program, operation 322 of reordering the decompressed all nucleotide sequence reads and all prediction quality information based on the respective corresponding identifiers, and operation 323 of producing the original genome sequencing data 310 by separating and then combining the reordered all nucleotide sequence reads and all prediction quality information from the respective corresponding identifiers.

The FASTQ data compression method according to an example embodiment may improve a compression ratio using a new reordering scheme (based on character frequency of nucleotide sequence) instead of using a conventional art (based on an overlapping ratio or lexicographic order). In particular, by adding a preprocessing process of verifying data, the FASTQ data compression method may improve stability to properly operate regardless of a size of genome sequencing data and a length of a nucleotide sequence. Therefore, the example embodiments may propose a first lossless compression method about prediction quality information (a portion of FASTQ format data).

Hereinafter, each operation of the FASTQ data compression method is further described by using the FASTQ data compression apparatus according to an example embodiment as an example.

Referring to FIG. 3, in operation 311, the genome sequencing data separator 210 may separate the genome sequencing data 310 into components of the identifier, the nucleotide sequence read, and the prediction quality information. The, genome sequencing data separator 210 may separate the identifier into a unique number of the identifier and additional information of the identifier. Here, the additional information of the identifier may be used as information of the identifier when performing compression through the compression program to generate the compressed genome sequencing data 320.

In operation 312, the character frequency measurer 220 may measure the character frequency for the entire data of each of the separated nucleotide sequence read and prediction quality information. Through this, a low distribution letter may be excluded and a priority may be assigned to each character in a subsequent score production operation. That is, the character frequency measurer 220 may measure a letter distribution for entire data of each of the nucleotide sequence read and prediction quality information and may exclude a corresponding letter if the measured letter distribution is below a threshold.

In operation 313, the score producer 230 may produce the score by applying the measured character frequency for the nucleotide sequence read and the prediction quality information. In detail, the score producer 230 may measure character frequency for a single nucleotide sequence read and produce a score, and may repeat scoring for all nucleotide sequence reads including repetition of the single nucleotide sequence read. The prediction quality information may be performed in the same manner. That is, the score producer 230 may measure character frequency for single prediction quality information and may produce a score, and may repeat scoring for all prediction quality information including repetition of the single prediction quality information.

The score producer 230 may produce a score based on at least one of priority information and exclusion target information obtained through the measured character frequency for the nucleotide sequence read and the prediction quality information and may produce a score using all a letter distribution value that is character frequency information and a distribution value that is obtained by rounding the letter distribution value.

In operation 314, the score-based sorter 240 may reorder the nucleotide sequence read and the prediction quality information based on the condition that is preset based on the score. In detail, the score-based sorter 240 may perform lexicographic order based on the produced score after combining all nucleotide sequence reads with the respective corresponding identifiers. Also, the score-based sorter 240 may combine the prediction quality information with the respective corresponding identifiers and may perform lexicographic order based on the produced score.

In operation 315, the genome sequencing data compressor 250 may compress at least one of information of the identifier, the identifier of the nucleotide sequence read, and the identifier of the prediction quality information by including the reordered nucleotide sequence read and the reordered prediction quality information and may generate the compressed genome sequencing data 320.

That is, the genome sequencing data compressor 250 may compress the additional information of the identifier, the reordered nucleotide sequence read, the reordered prediction quality information, the identifier of the nucleotide sequence read, and the identifier of the prediction quality information through the compression program. Here, the genome sequencing data compressor 250 may store the reordered nucleotide sequence read in combination with the identifier of the nucleotide sequence read through the compression program to remember order, and may store the reordered prediction quality information in combination with the identifier of the prediction quality information through the compression program.

Also, the compressed genome sequencing data 320 may be decompressed through the decompressor.

In operation 321, the decompressor may decompress the compressed genome sequencing data 320 using the compression program.

In operation 322, the decompressor may reorder the decompressed all nucleotide sequence reads and all prediction quality information based on the respective corresponding identifiers.

In operation 323, the decompressor may generate the original genome sequencing data 310 by separating and then combining the reordered all nucleotide sequence reads and all prediction quality information from the respective corresponding identifiers.

Hereinafter, a FASTQ data compression method and apparatus according to an example embodiment are further described.

Separation of Genome Sequencing Data for Each Component

Figure 4:
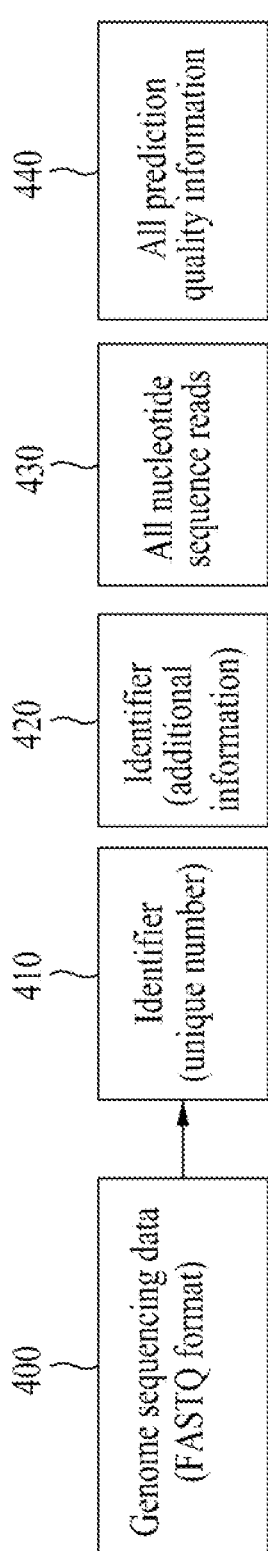
FIG. 4 illustrates an example of describing a process of separating genome sequencing data for each component according to an example embodiment.

FIG. 4 illustrates an example of describing a process of separating genome sequencing data for each component according to an example embodiment.

A FASTQ format of genome sequencing data refers to a single type of a text format and is specialized for storing the genome sequencing data. The genome sequencing data stored in the FASTQ format is a set of nucleotide sequences (read). In the FASTQ format, each nucleotide sequence (read) includes an identifier (identifier), a nucleotide sequence read (sequence), and prediction quality information (quality). Here, in the case of the identifier, each of all nucleotide sequences in front of a first blank stores a unique number with a different value and each of all nucleotide sequence at the rear of the first blank includes similar or identical additional information. Therefore, the genome sequencing data may include a total of four components. Here, since a letter type and a number of letters used for each component differ and have a different meaning, a separately compressing method is efficient. Referring to FIG. 4, this program may separate and thereby store genome sequencing data 400 into at least one of a unique number 410 of an identifier, additional information 420 of the identifier, all nucleotide sequence reads 430, and all prediction quality information 440.

Measurement of Character Frequency for all Nucleotide Sequences

All nucleotide sequence reads mostly include A, C, G, T, and N. However, since it is indicated using 0, 1, 2, and 3 depending on a device that produces genome sequencing data, a process of verifying a letter (character) type is required. This process refers to a process of verifying a percentage of a letter in all nucleotide sequence reads and defines a letter and priority to be used for a subsequent score production operation.

Figure 5A:
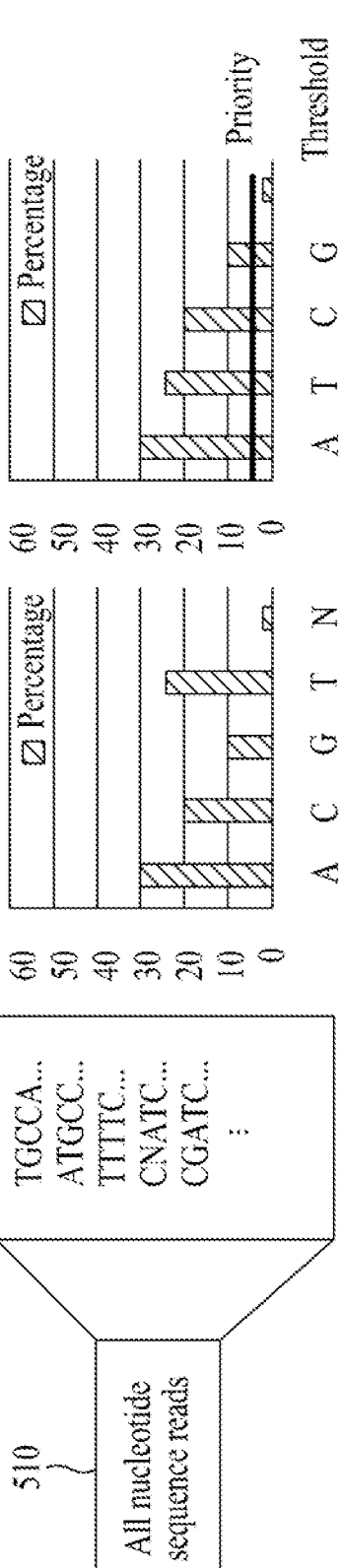
FIG. 5A illustrates an example of describing a character frequency measurement process for all nucleotide sequences according to an example embodiment.
Figure 5B:
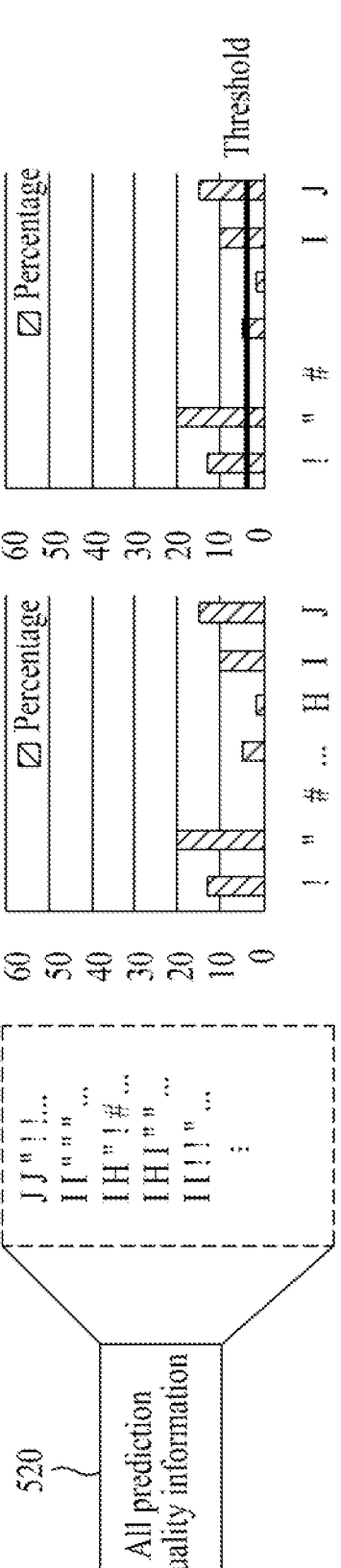
FIG. 5B illustrates an example of describing a character frequency measurement process for all prediction quality information according to an example embodiment.

FIG. 5A illustrates an example of describing a character frequency measurement process for all nucleotide sequences according to an example embodiment, and FIG. 5B illustrates an example of describing a character frequency measurement process for all prediction quality information according to an example embodiment.

Referring to FIG. 5A, in all nucleotide sequence reads 510, if N's percentage is below a threshold, N is not considered in a subsequent operation. The higher the percentage, the higher priority is assigned and a corresponding letter is used in a subsequent score production operation. Here, for example, 5% may be used as a threshold based on all nucleotide sequence reads 510.

Although a short nucleotide sequence (short-read) generally includes 40 letters, a recent device uses eight or four letters. A long nucleotide sequence (long-read) includes a number of letters greater than that of the short nucleotide sequence.

Referring to FIG. 5B, the all prediction quality information 520 includes a number of letters greater than that of all nucleotide sequence reads 510. Therefore, a score may be produced in the same manner as the all nucleotide sequence reads 510. However, a smaller value may be used as a threshold. For example, 1% may be used as a threshold of the all prediction quality information 520 based on the all prediction quality information 520. Unlike categorical nucleotide sequence read data, prediction quality information relates to discrete data and thus does not use priority made by percentage.

Producing a Score Based on a Single Nucleotide Sequence

All nucleotide sequence reads include repletion of single nucleotide sequence read. This program repeats a single nucleotide sequence read-based score production method for all nucleotide sequence reads. The single nucleotide sequence read-based score production method uses priority and exclusion target information acquired through measuring of character frequency for previous all nucleotide sequences. Since lexicographic order is performed subsequently, higher priority represents that it is present relatively in front when producing a score. The score may be produced based on character frequency of a single nucleotide sequence read and a rounded distribution may be used together. Here, the rounded distribution may be used since if only an existing distribution is used, a letter having top priority affects most.

Figure 6:
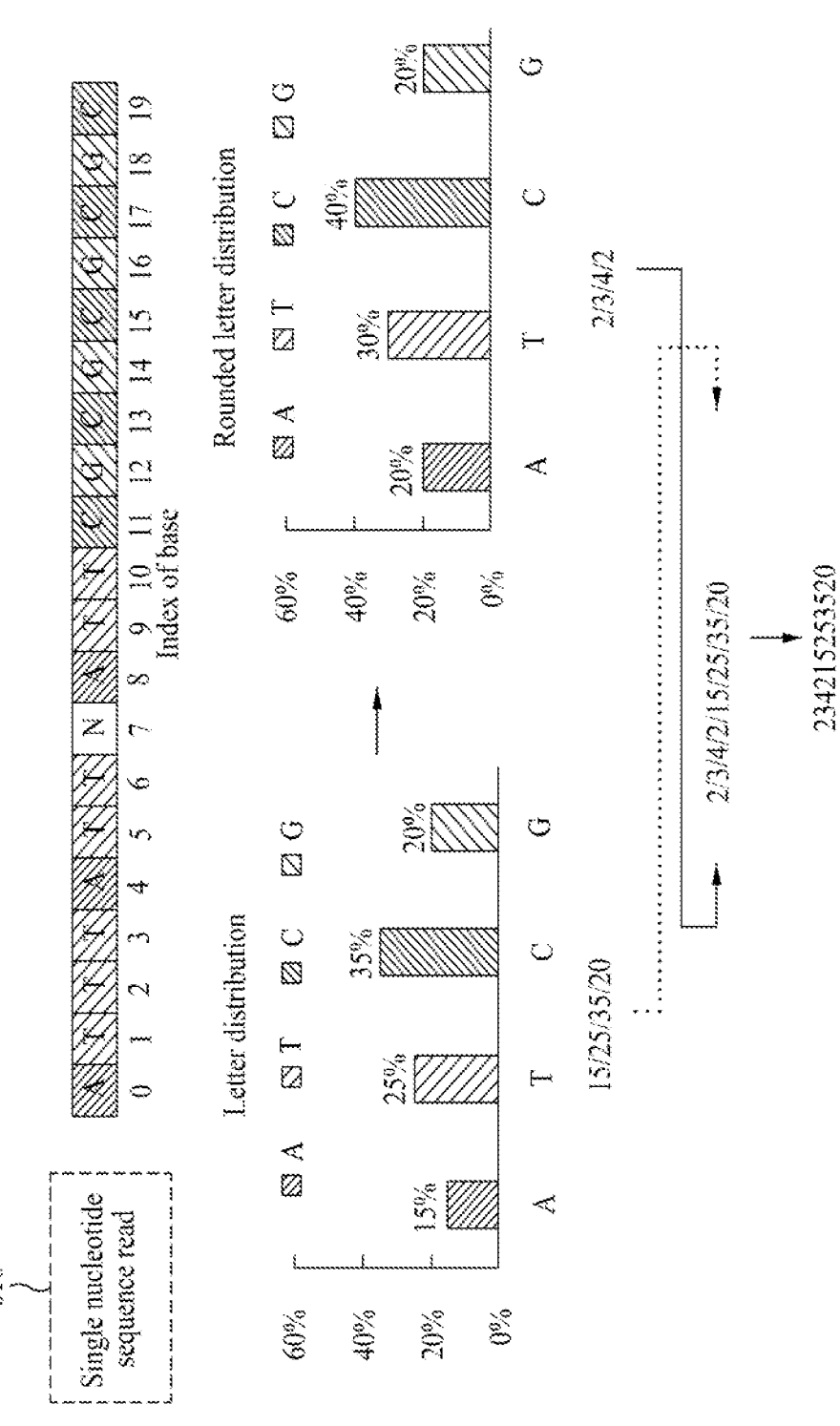
FIG. 6 illustrates an example of describing a letter distribution of a single nucleotide sequence according to an example embodiment.

FIG. 6 illustrates an example of describing a letter distribution of a single nucleotide sequence according to an example embodiment.

If character frequency of a single nucleotide sequence read is composed as illustrated in FIG. 5A, N is a target to be excluded and priority is in order of A, T, C, and G. For example, with the assumption that letter distributions of A, T, C, and G in a single nucleotide sequence read 610 are 15%, 25%, 35%, and 20%, respectively, as illustrated in FIG. 6, rounded distributions may be 20%, 30%, 40%, and 20%.

Figure 7A:
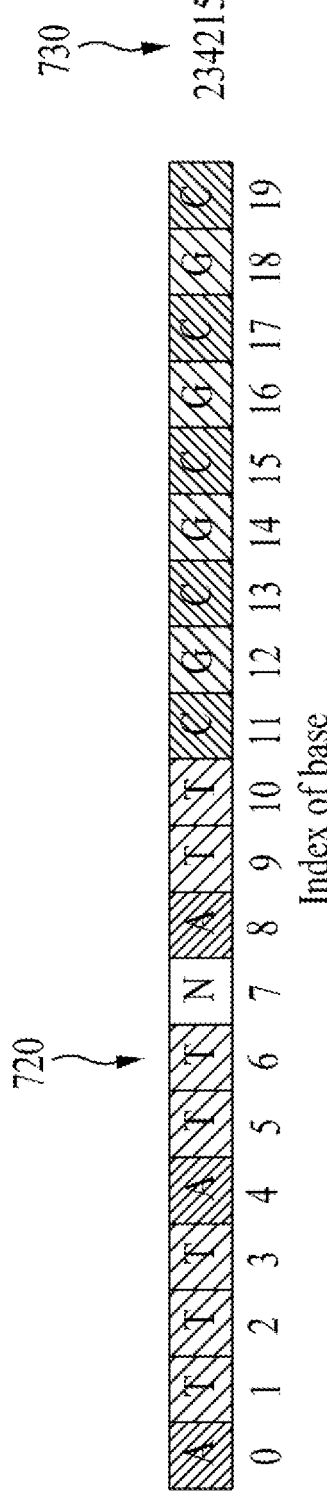
FIG. 7A illustrates an example of score production using character frequency of a single nucleotide sequence read according to an example embodiment.
Figure 7B:
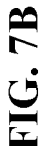
FIG. 7B illustrates an example of score production using character frequency of all nucleotide sequence reads according to an example embodiment.

FIG. 7A illustrates an example of score production using character frequency of a single nucleotide sequence read according to an example embodiment. Also, FIG. 7B illustrates an example of score production using character frequency of all nucleotide sequence reads according to an example embodiment.

Referring to FIG. 7A, a score 730 of a single nucleotide sequence read 720 may be produced using a front digit of a rounded distribution of a letter distribution and the letter distribution. For example, a score of a single nucleotide sequence read as described with FIG. 6 has a value of 234215253520 through sequential reordering using the rounded distributions 20%, 30%, 40%, and 20% and the original letter distribution. If it is repeated to all nucleotide sequence reads 720 according to the respective identifiers 710, scores 730 of all nucleotide sequence reads 720 as illustrated in FIG. 7B may be obtained. Scores of all prediction quality information may be produced in the same manner.

Ordering of Score-Based all Nucleotide Sequences

Figure 8A:
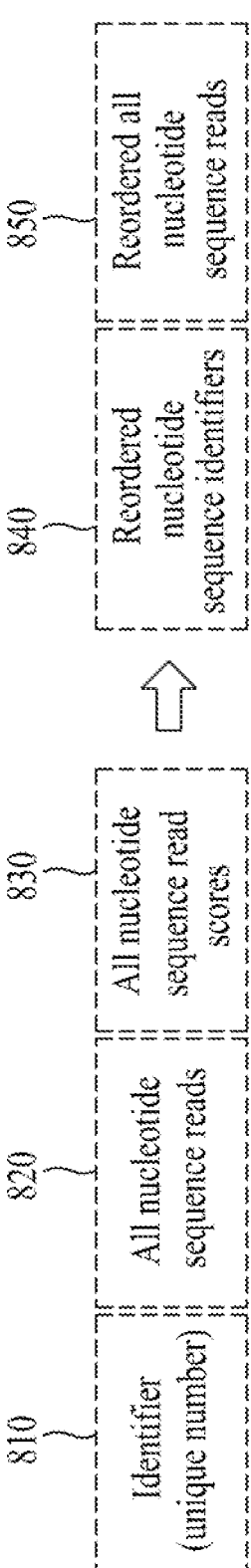
FIG. 8A illustrates an example of describing lexicographic order of score-based all nucleotide sequence reads according to an example embodiment.
Figure 8B:
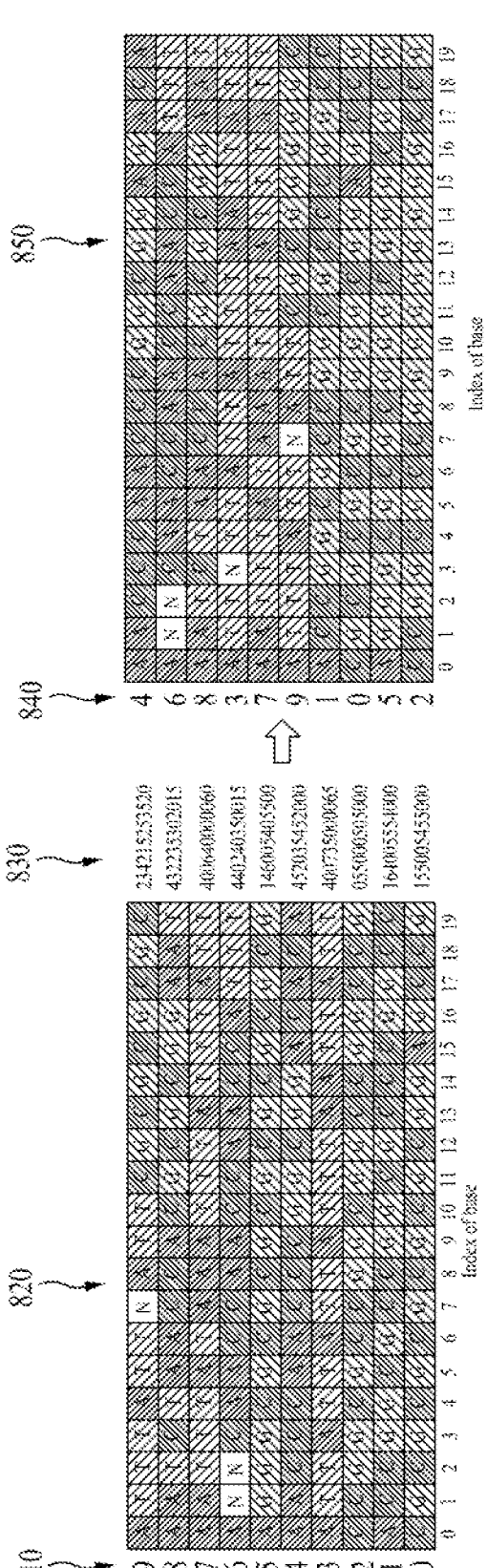
FIG. 8B illustrates an example of lexicographic order of score-based all nucleotide sequence reads according to an example embodiment.

FIG. 8A illustrates an example of describing lexicographic order of score-based all nucleotide sequence reads according to an example embodiment. Also, FIG. 8B illustrates an example of lexicographic order of score-based all nucleotide sequence reads according to an example embodiment.

As illustrated in FIG. 8A, to restore subsequent order, a unique number 810 of an identifier before being reordered is combined with all nucleotide sequence reads 820. All nucleotide sequence reads 820 are reordered based on all nucleotide sequence read scores 830 obtained through a previous process. A reordering method is simple lexicographic order and arranges first all nucleotide sequence reads 820 with a higher score.

After reordering, the all nucleotide sequence read scores 830 are not separately stored to improve a compression ratio. Accordingly, after reordering, they may be represented as reordered nucleotide sequence identifiers 840 and reordered all nucleotide sequence reads 850. All prediction quality information may be reordered in the same manner as that of the all nucleotide sequence reads 820. That is, FIG. 8B may represent an example of lexicographic order of score-based all nucleotide sequence reads.

This reordering method differs from general lexicographic order used in a genome sequencing data compression scheme. The general lexicographic order does not consider the entire character frequency. Therefore, in many cases, order of a corresponding nucleotide sequence may be determined by a letter that appears first.

Figure 9A:
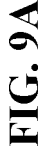
FIG. 9A illustrates an example of score-based order according to an example embodiment.

FIG. 9A illustrates an example of score-based order according to an example embodiment. Also, FIG. 9B illustrates an example of lexicographic order according to an example embodiment.

Figure 9B:
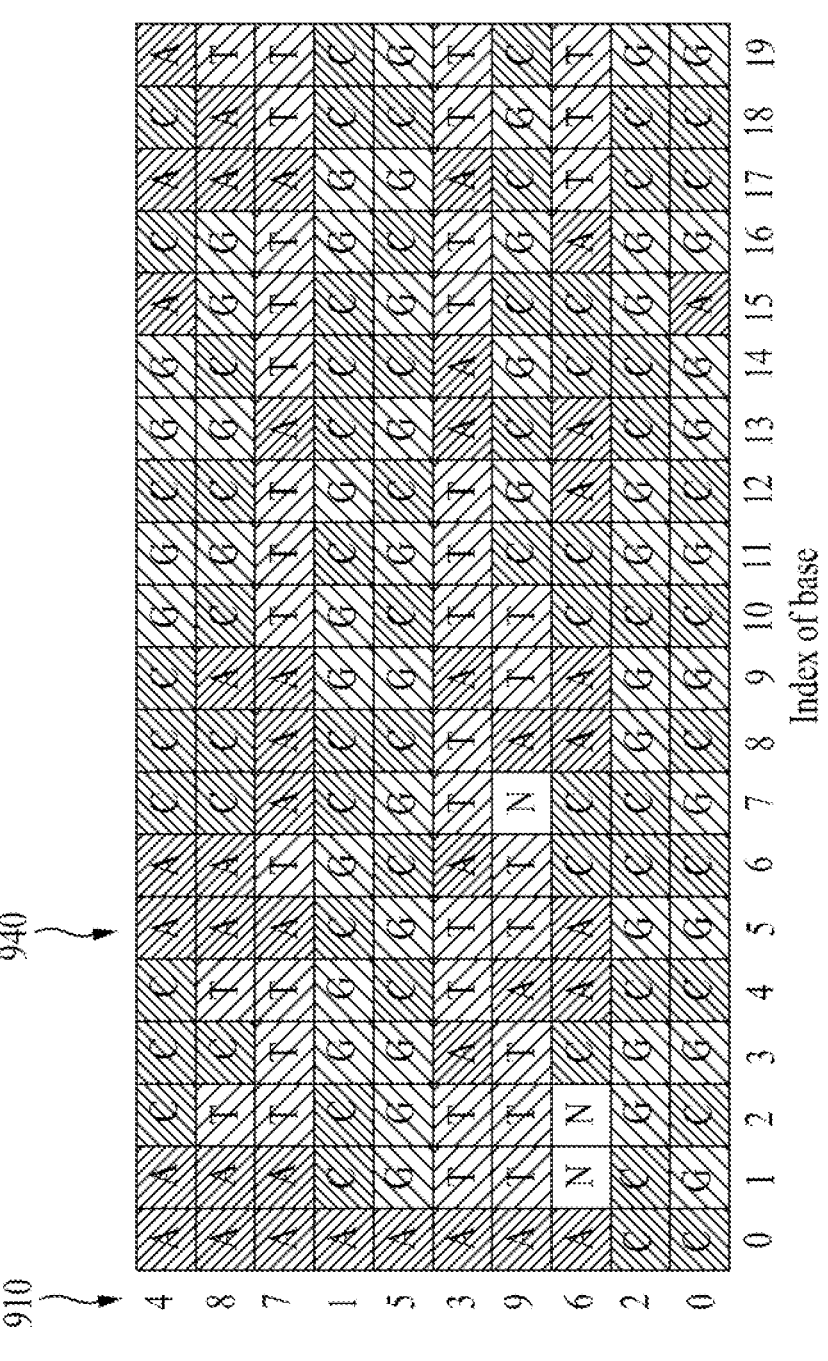
FIG. 9B illustrates an example of lexicographic order according to an example embodiment.

Referring to FIGS. 9A and 9B, score-based reordering results and lexicographic order results may be compared. For example, with the assumption that all nucleotide sequence reads 940 are composed as illustrated in FIG. 9B, they may be reordered based on letters that appear first. Therefore, it can be verified that a nucleotide sequence with identifier 7 and a nucleotide sequence with identifier 3 are very similar, but are separate from each other after reordering. However, this issue may be solved by using a score-based reordering method of FIG. 9A. Here, 910 may represent identifiers, 920 may represent all nucleotide sequence reads, and 930 may represent scores of all nucleotide sequence reads.

Compression Program

This program regards a compression ratio more important than a compression speed and thus, may use a compression program, for example, ZPAQ. This method is similar to a method frequently used to improve a compression ratio in the existing study for compression of genome sequencing data. This method uses LZ77 as data preprocessing, which may improve a compression ratio through reordering. Therefore, the method is used herein. In a data preprocessing process, a compression ratio may be improved by reordering a nucleotide sequence read and prediction quality information and each of the nucleotide sequence read and the prediction quality information is stored through the compression program. To remember order, the nucleotide sequence read is stored in combination with an identifier of the nucleotide sequence read and prediction quality information is also stored with a corresponding identifier. They may be used in a subsequent decompression process. Additional information of the separated each identifier is stored.

Decompression

A decompression method proposed in FASTQ_CLS may include the following stages. First, a compressed part may be decompressed using a compression program, for example, ZPAQ. Second, all nucleotide sequence reads may be decompressed in original order through identifiers of reordered nucleotide sequence reads. All prediction quality information may be decompressed in original order through identifiers of reordered prediction quality information. Third, the decompressed all nucleotide sequence reads and the decompressed prediction quality information may be separated from the respective corresponding identifiers. Fourth, an original FASTQ format may be generated by combining the separated all nucleotide sequence reads with all prediction quality information, the identifiers, and additional information of the identifiers.

The example embodiments employ a method of reordering character frequency-based sequences. Existing technology for improving a compression ratio of genome sequencing data through reordering currently show good performance. This technology employs a method of finding and reordering a longest overlapping area between nucleotide sequence reads. Such methods may not properly operate in a variable length or may have degraded performance. Therefore, the following example embodiments employ a method of measuring and comparing character frequency instead of employing the method of finding and reordering a longest overlapping area between nucleotide sequence reads. Through this, the example embodiments may execute an accurate operation by inducing a type of genome sequencing data. Also, while the existing technology may operate only in a nucleotide sequence read having a large common area, the example embodiments may execute reordering even on prediction quality information. A new lossless compression method may be provided for prediction quality information that has been studied depending only on loss compression. Through this method, it is possible to produce a FASTQ data compression program that stably operates regardless of a production platform and a size of data.

Genome sequencing data in the past has used short nucleotide sequencing data. However, due to current limitations of short nucleotide sequencing data, long nucleotide sequencing data has appeared. Due to development of such technology, experiments on larger organisms are being conducted, which is a factor that increases a size of data. Further, short nucleotide sequencing data is also longer than data generated in the past and a prediction quality score value of a nucleotide sequence uses a smaller number of types. Therefore, there are some constraints in testing using a compression method using only short nucleotide sequencing data.

Therefore, the example embodiments have performed experiments by adding newly generated data beyond the existing standard benchmark data. As results of the experiments, this program operates well up to data having a nucleotide sequence length of 17,861 bp and also operates well in a file with a maximum size of 164,432 MB. Also, the example embodiments show the overall high results in terms of compression performance and show the highest compression ratio for data after 3G sequencing.

According to the example embodiments, it is possible to provide a program that stably operates in various genome sequencing data and shows good performance for recent generated data.

The apparatuses described herein may be implemented using hardware components, software components, and/or a combination thereof. For example, the apparatuses and the components described herein may be implemented using one or more general-purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and/or data may be embodied in any type of machine, component, physical equipment, virtual equipment, computer storage medium or device, to be interpreted by the processing device or to provide an instruction or data to the processing device. The software also may be distributed over network coupled computer systems so that the software is stored and executed in a distributed fashion. The software and data may be stored by one or more computer readable storage media.

The methods according to the above-described example embodiments may be configured in a form of program instructions performed through various computer devices and recorded in non-transitory computer-readable media. The media may also include, alone or in combination with the program instructions, data files, data structures, and the like. The program instructions recorded in the media may be specially designed and configured for the example embodiments or may be known to those skilled in the computer software art and thereby available. Examples of the media include magnetic media such as hard disks, floppy disks, and magnetic tapes; optical media such as CD-ROM and DVDs; magneto-optical media such as floptical disks; and hardware devices that are specially configured to store program instructions, such as read-only memory (ROM), random access memory (RAM), flash memory, and the like. Examples of program instructions include both machine code, such as produced by a compiler, and files containing higher level code that may be executed by the computer using an interpreter.

While this disclosure includes specific example embodiments, it will be apparent to one of ordinary skill in the art that various alterations and modifications in form and details may be made in these example embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of compressing genome sequencing data in FASTQ format through character frequency-based sequence reordering implemented by a computer apparatus, the method comprising:
providing a computer having a processor and a memory coupled to the processor, wherein the memory contains genome sequencing data in FASTQ format;

using the processor to separate the genome sequencing data into components of an identifier, a nucleotide sequence read, and prediction quality information;
using the processor to measure character frequency for the entire data of each of the nucleotide sequence read and the prediction quality information and omitting any nucleotide having a first percentage frequency below a first threshold and any prediction quality having a second percentage frequency information below a second threshold;
using the processor to produce a score for each nucleotide read that is comprised of a front digit from a rounded distribution of each letter distribution in the genome sequencing data and the letter distribution in the genome sequencing data from the measured character frequency for the nucleotide sequence read and the prediction quality information;
using the processor to reorder the nucleotide sequence read and the prediction quality information based on the score; and
using the processor to compress at least one of information of the identifier, an identifier of the nucleotide sequence read, and an identifier of the prediction quality information through a compression program by including the reordered nucleotide sequence read and the reordered prediction quality information and generating compressed genome sequencing data.

2. The method of claim 1, wherein the separating of the genome sequencing data comprises separating again the identifier into a unique number of the identifier and additional information of the identifier, and
the additional information of the identifier is used as information of the identifier when performing compression through the compression program to generate the compressed genome sequencing data.

3. The method of claim 1, wherein the producing of the score comprises:
measuring character frequency for a single nucleotide sequence read and producing a score; and
repeating scoring for all nucleotide sequence reads including repetition of the single nucleotide sequence read.

4. The method of claim 1, wherein the producing of the score comprises:
measuring character frequency for single prediction quality information and producing a score; and
repeating scoring for all prediction quality information including repetition of the single prediction quality information.

5. The method of claim 1, wherein the producing of the score comprises producing a score based on at least one of priority information and exclusion target information obtained through the measured character frequency for the nucleotide sequence read and the prediction quality information, and producing a score using all a letter distribution value that is character frequency information and a distribution value that is obtained by rounding the letter distribution value.

6. The method of claim 3, wherein the reordering of the nucleotide sequence read and the prediction quality information comprises combining the all nucleotide sequence reads with the respective corresponding identifiers and performing lexicographic order based on the produced score.

7. The method of claim 4, wherein the reordering of the nucleotide sequence read and the prediction quality information comprises combining the prediction quality information with the identifier and performing lexicographic order based on the produced score.

8. The method of claim 1, wherein the generating of the compressed genome sequencing data comprises storing the reordered nucleotide sequence read in combination with an identifier of the nucleotide sequence read through the compression program to remember order and storing the reordered prediction quality information in combination with an identifier of the prediction quality information through the compression program.

9. The method of claim 1, further comprising:

decompressing the compressed genome sequencing data through the compression program;

reordering the decompressed all nucleotide sequence reads and all prediction quality information based on the respective corresponding identifiers; and producing original genome sequencing data by separating and then combining the reordered all nucleotide sequence reads and all prediction quality information from the respective corresponding identifiers.

10. An apparatus for compressing genome sequencing data in FASTQ format through character frequency-based sequence reordering implemented by a computer apparatus, the apparatus comprising:

a computer having a processor and a memory coupled to the processor, wherein the memory contains genome sequencing data and wherein the processor is programmed to include a genome sequencing data separator configured to separate the genome sequencing data into components of an identifier, a nucleotide sequence read, and prediction quality information;

wherein the processor is further programmed to include a character frequency measurer configured to measure character frequency for the entire data of each of the nucleotide sequence read and the prediction quality information and omitting any nucleotide having a first percentage frequency below a first threshold and any prediction quality having a second percentage frequency information below a second threshold;

wherein the processor is further programmed to include a score producer configured to produce a score for each nucleotide read that is comprised of a front digit from a rounded distribution of each letter distribution in the genome sequencing data and the letter distribution in the genome sequencing data from the measured character frequency for the nucleotide sequence read and the prediction quality information;

wherein the processor is further programmed to include a score-based sorter configured to reorder the nucleotide sequence read and the prediction quality information based on the score; and wherein the processor is further programmed to include a genome sequencing data compressor configured to compress at least one of information of the identifier, an identifier of the nucleotide sequence read, and an identifier of the prediction quality information through a compression program by including the reordered nucleotide sequence read and the reordered prediction quality information and to generate compressed genome sequencing data.

11. The apparatus of claim 10, wherein the genome sequencing data separator is configured to separate again the identifier into a unique number of the identifier and additional information of the identifier, and the additional information of the identifier is used as information of the identifier when performing compression through the compression program to generate the compressed genome sequencing data.

12. The apparatus of claim 10, wherein the character frequency measurer is configured to measure a letter distribution for the entire data of each of the nucleotide sequence read and the prediction quality information and excluding a corresponding letter if the measured letter distribution is below a threshold.

13. The apparatus of claim 10, wherein the score producer is configured to measure character frequency for a single nucleotide sequence read and produce a score, and to repeat scoring for all nucleotide sequence reads including repetition of the single nucleotide sequence read.

14. The apparatus of claim 10, wherein the score producer is configured to measure character frequency for single prediction quality information and produce a score, and to repeat scoring for all prediction quality information including repetition of the single prediction quality information.

15. The apparatus of claim 10, wherein the score producer is configured to produce a score based on at least one of priority information and exclusion target information obtained through the measured character frequency for the nucleotide sequence read and the prediction quality information, and to produce a score using all a letter distribution value that is character frequency information and a distribution value that is obtained by rounding the letter distribution value.

16. The apparatus of claim 13, wherein the score-based sorter is configured to combine the all nucleotide sequence reads with the respective corresponding identifiers and to perform lexicographic order based on the produced score.

17. The apparatus of claim 14, wherein the score-based sorter is configured to combine the prediction quality information and the identifier and to perform lexicographic order based on the produced score.

18. The apparatus of claim 10, wherein the genome sequencing data compressor is configured to store the reordered nucleotide sequence read in combination with an identifier of the nucleotide sequence read through the compression program to remember order and to store the reordered prediction quality information in combination with an identifier of the prediction quality information through the compression program.

19. The apparatus of claim 10, further comprising:

a genome sequencing data decompressor configured to decompress the compressed genome sequencing data through the compression program, to reorder the decompressed all nucleotide sequence reads and all prediction quality information based on the respective corresponding identifiers, and to produce original genome sequencing data by separating and then combine the reordered all nucleotide sequence reads and all prediction quality information from the respective corresponding identifiers.

* * * * *